United States Patent [19]

Carroll et al.

[11] Patent Number: 4,804,485

[45] Date of Patent: Feb. 14, 1989

[54] POLYALKYLENEOXYAMINE CATALYSTS FOR DIALKYL DISULFIDES AND/OR POLYSULFIDES USED IN DISSOLVING SULFUR

[75] Inventors: Glenn T. Carroll, Jeffersonville; Michael J. Lindstrom, Downingtown; William J. Tuszynski, Spinnerstown, all of Pa.

[73] Assignee: Pennwalt Corporation, Philadelphia, Pa.

[21] Appl. No.: 47,956

[22] Filed: May 8, 1987

[51] Int. Cl.$^4$ .......................... E21B 37/00; B08B 9/02
[52] U.S. Cl. ................................ 252/8.552; 166/312; 299/5; 568/21
[58] Field of Search ...................... 252/8.552; 299/4, 5; 166/312; 568/21; 502/167

[56] References Cited

U.S. PATENT DOCUMENTS

| | | | |
|---|---|---|---|
| 2,470,830 | 5/1949 | Monson | 252/8.552 |
| 3,531,160 | 9/1970 | Fisher | 299/5 |
| 3,545,916 | 12/1970 | Deicher et al. | |
| 3,835,927 | 9/1974 | Oude Alink et al. | 166/304 |
| 3,846,311 | 11/1974 | Sharp et al. | 252/8.552 |
| 3,909,422 | 9/1975 | Sample, Jr. et al. | 252/8.552 |
| 4,033,410 | 7/1977 | Kauffman | |
| 4,230,184 | 10/1980 | Blytas | 166/312 |
| 4,239,630 | 12/1980 | Atkinson et al. | 252/8.552 |
| 4,248,717 | 2/1981 | Sharp et al. | 252/8.552 |
| 4,290,900 | 9/1981 | Sharp et al. | 252/8.552 |
| 4,295,979 | 10/1981 | Sharp et al. | 252/8.555 |
| 4,350,600 | 9/1982 | Sharp et al. | 252/8.555 |
| 4,379,490 | 4/1983 | Sharp | 166/304 |

FOREIGN PATENT DOCUMENTS

| | | |
|---|---|---|
| 974912 | 9/1975 | Canada . |
| 2152532 | 4/1973 | France . |
| 2573991 | 6/1986 | France . |
| 2579203 | 9/1986 | France . |
| 2579585 | 10/1986 | France . |

OTHER PUBLICATIONS

Clark et al., "The Composition of Merox-Oily Disulfide Mixtures", ASRL Quarterly Bulletin, vol. XVIII, No's. 2, 3 & 4 (1982), pp. 44+.

Clark et al., "New Catalysts for Merox Solutions, Etc.", ASRL Quarterly Bulletin, vol. XIX, No's. 1 & 2 (1982), p. 4+.

*Primary Examiner*—Herbert B. Guynn

[57] ABSTRACT

A composition, useful for dissolving sulfur, which comprises a major amount of a disulfide or polysulfide and a catalyst comprising one or more polyalkyleneoxyamines or polyamines, and methods for using the composition in a system to prevent sulfur-plugging, are disclosed.

24 Claims, No Drawings

POLYALKYLENEOXYAMINE CATALYSTS FOR DIALKYL DISULFIDES AND/OR POLYSULFIDES USED IN DISSOLVING SULFUR

BACKGROUND

This invention relates to a composition of matter which is a liquid disulfide, polysulfide or mixture of these incorporating a catalytic amount of a polyalkyleneoxyamine, a polyalkyleneoxypolyamine or mixtures thereof to provide a material capable of dissolving unexpectedly large amounts of sulfur at a high rate. It also relates to a process for dissolving sulfur utilizing such composition. Additionally, it relates to a process for preparing polysulfides by reacting a disulfide or low rank polysulfide with sulfur in the presence of one or more of the herein disclosed catalysts.

In the procesing of sour gas wells, sulfur may form deposits that can plug the well and terminate production. These deposits have been prevented or dissolved by flowing solvents such as carbon disulfide, mineral and spindle oils, organic solvents, and aqueous alkylamines downhole to dissolve the sulfur plug. The solvent is injected downhole and the well is allowed to soak for a sufficient amount of time to dissolve any existing sulfur plugs. Alternatively, the solvent can be injected continuously in amounts sufficient to prevent the formation of sulfur deposits. The above systems all have various disadvantages such as toxicity, flammability, corrosivity, and limited ability to dissolve sulfur.

PRIOR ART

Dialkyl disulfides, either alone or blended with dialkyl sulfides (U.S. Pat. No. 3,531,160), have become the sulfur solvent of choice. Hyne [Alberta Sulfur Research Ltd. (ASRL), Quarterly Bulletin, Vol. XVIII, Nos. 2, 3, and 4, 1982, p. 44] has shown that lower dialkyl disulfides, especially dimethyl disulfide (DMDS) are preferred. Alone, they take up only a limited amount of sulfur; however, in conjunction with a suitable catalyst system they can take up approximately 1.5 times their weight in sulfur at room temperature.

Sharp and Sudduth (U.S. Pat. No. 3,846,311) teach that a composition of one or more dialkyl disulfides and an unsubstituted, saturated, aliphatic amine (up to 10 wt%) is capable of consuming over 200 wt% sulfur after the composition has been aged. French Patents FR Nos. 2,152,532 and FR 2,159,320 claim similar compositions without aging where the amine is any aliphatic amine. It is also disclosed in the art that if a small amount of sulfur (5-40 wt%) is added to the above compositions the rate of sulfur uptake is accelerated (U.S. Pat. No. 4,239,630).

In deep wells, where temperatures greater than 250° F. may be reached, Sharp and Yarborough (U.S. Pat. No. 4,290,900) teach that the composition is not as effective if vaporization occurs. Therefore, they disclose the use of a composition of a dialkyl disulfide and a fatty acid amine (>30 wt%) which also has been aged. Further, the art teaches that the addition of 60 wt% sulfur to the above composition accelerates sulfur uptake (U.S. Pat. No. 4,248,717).

Hyne and coworkers (ASRL Quarterly Bulletin, Vol. XIX, Nos. 1 & 2, 1982, p. 4) showed that sodium hydrosulfide (NaSH) and dimethylformamide (used as a cosolvent) is an effective system for catalyzing sulfur uptake by dimethyl disulfide. They also demonstrated that a variety of alkali salts of a series of thiophenols, in conjunction with dimethylformamide (DMF), catalyzes sulfur-uptake. It is known that the sulfur-recovery systems of Hyne et al. have one major disadvantage; they are unstable and lose activity within 3-10 days upon standing at room temperature.

STATEMENT OF THE INVENTION

This invention is a composition comprising a major proportion of a disulfide, polysulfide or mixture of these sulfides having the following formula:

$$R^1SS_aSR^2$$

where $R^1$ and $R^2$ are independently alkyl, alkaryl (eg. tolyl), alkoxyalkyl (eg. ethoxyethyl), or hydroxyalkyl (eg. hydroxyethyl) radicals wherein the alkyl moiety has from 1 to 24 carbon atoms and $a$ is the average number of internal sulfur atoms in the sulfide and ranges from 0 to 3, and a catalytic amount of one or more polyalkyleneoxyamines or -polyamines containing a primary or secondary amine functionality and wherein the alkylene radical is a substituted or unsubstituted alkylene radical having from 2 to 22 carbon atoms.

This invention is also a process utilizing the above-defined composition for dissolving sulfur in a system, particularly in oil or gas wells having high sulfur deposits and in pipelines and other equipment which are subject to plugging with sulfur.

Furthermore, this invention is a process for preparing polysulfides by reacting disulfides or low rank polysulfides with sulfur in the presence of one or more of the above-defined polyalkyleneoxyamines or -polyamines.

DETAILED DESCRIPTION OF THE INVENTION

This invention is a superior composition for dissolving sulfur. The composition may be used whenever a requirement for sulfur removal exists. One such application is to dissolve or prevent sulfur plugs in sour and super-sour oil and gas wells.

A disulfide or a polysulfide of a low sulfur rank can be used for the composition of this invention. The sulfur rank is defined as the average of the number of sulfur atoms between the two alkyl groups in a mixture of di- and polysulfides. A rank greater than 2 but less than 3 is considered low. A low sulfur rank is preferred since a sulfur rank greater than 3 will have a limited capacity to take up additional sulfur.

The formulas 1, 2, 3, and 4 shown below are given as examples to demonstrate the types of polyalkyleneoxyamines and -polyamines that will act as catalsts for sulfur-uptake by disulfides or polysulfides of low sulfur rank.

(1)

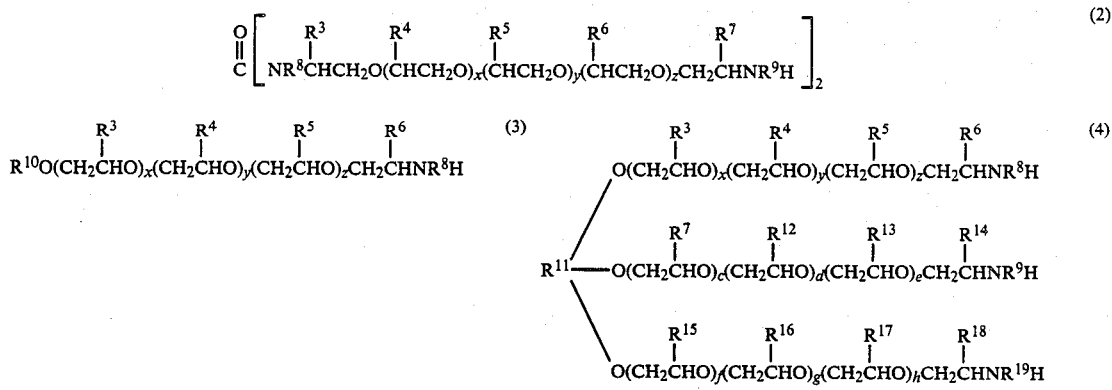

where $R^3$, $R^4$, $R^5$, $R^6$, $R^7$, $R^{10}$, $R^{12}$, $R^{13}$, $R^{14}$, $R^{15}$, $R^{16}$, $R^{17}$, and $R^{18}$ are independently H, alkyl, alkaryl, hydroxyalkyl, alkoxyalkyl, haloalkyl, wherein the alkyl moieties have from 1 to 20 carbon atoms, or phenyl; $R^8$, $R^9$, and $R^{19}$ are independently H, alkyl, hydroxyalkyl, alkoxyalkyl, alkaryl wherein the alkyl moieties have from 1 to 10 carbon atoms, aryl, or $CONH_2$; $R^{11}$ is the hydrocarbon residue of a triol; and b, c, d, e, f, g, h, x, y, and z are independently values of 0–200, provided, however, that the total of such values is no less than 2. The catalytic amount of the polyalkyleneoxyamine and/or polyamine can range in concentration from an amount small enough to be effective (e.g., 100 parts/million) to 10 wt%.

Jeffamines ®, a series of polyalkyleneoxyamines produced by the Texaco Chemical Company, are but one example encompassed by the above formulas. Furthermore, any polyalkyleneoxy-compound which contains a primary or secondary amine functionality will be active. Additionally, formula 4 shows the hydrocarbon residue of a triol, such as glycerol; ($R^{11}$) as the base of the compound, although any other similar polyalkyleneoxyamine which incorporates any polyol as its base should also be effective.

Examples of Jeffamine ® products which are preferred for this invention include those identified below under the alpha-numeric product designation.

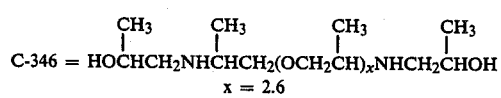

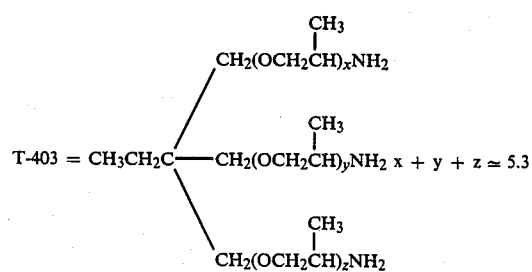

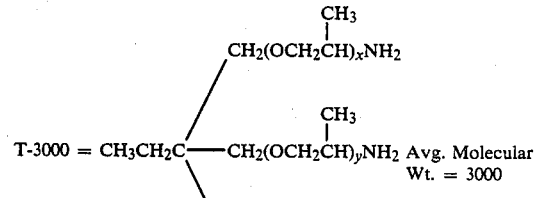

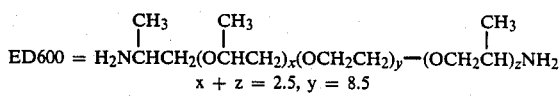

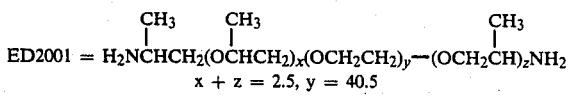

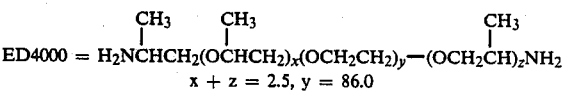

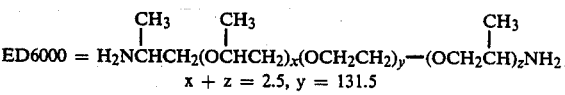

EDR-148 = $H_2NCH_2CH_2OCH_2CH_2OCH_2CH_2NH_2$
EDR-192 = $H_2NCH_2CH_2OCH_2CH_2OCH_2CH_2OCH_2CH_2NH_2$

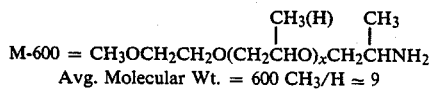

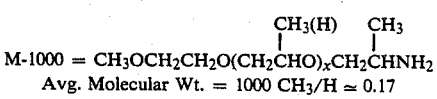

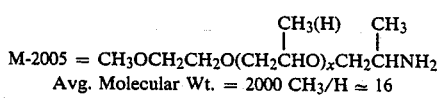

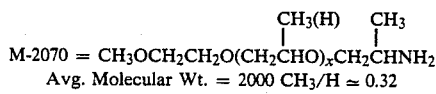

M-2070 = CH₃OCH₂CH₂O(CH₂CHO)ₓCH₂CHNH₂ with CH₃(H) and CH₃ substituents
Avg. Molecular Wt. = 2000 CH₃/H ≈ 0.32

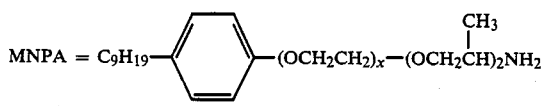

MNPA = C₉H₁₉—(phenyl)—(OCH₂CH₂)ₓ—(OCH₂CH)₂NH₂ with CH₃ substituent

MNPA-380 = Avg. Molecular Wt. = 380
MNPA-510 = Avg. Molecular Wt. = 510
MNPA-750 = Avg. Molecular Wt. = 750

Optionally, an aliphatic amine, an aryl amine, an alkaryl amine, or an alkanolamine wherein the aliphatic alkyl moieties have from 1 to 24 carbon atoms or their respective ethers can be added to the compositions, alone or in mixtures, to increase activity. These amine are not as active as the polyalkyleneoxyamines; however, a composition which contains an additional amount of said amine will possess a greater activity for sulfur-uptake than an identical composition that does not contain said amine. Said amines may be used in cases where their cost is lower than the cost of the polyalkyleneoxyamine to give a composition of comparable activity but lower cost.

The compositions may have their activity enhanced by activation with H₂S and/or a C₁–C₂₄ alkyl, alkoxyalkyl, hydroxyalkyl, alkaryl, or an aryl mercaptan. High activity results in sour gas and oil wells without pretreatment of the composition with H₂S, since it is well known that sour and super-sour gas and oil wells which plug with sulfur contain H₂S. The use of said compositions in other applications, where H₂S is not present, may require pretreatment with H₂S and/or said mercaptan to dissolve sulfur or enhance the rate of sulfur-uptake. If activation by H₂S and/or a volatile mercaptan is desired, then the activated composition can be, optionally, purged with nitrogen to remove residual H₂S and/or mercaptan. The amount of H₂S and/or said mercaptan may range from an amount large enough to be effective to 10 wt%. Amounts as small as 0.05 wt% have been found to be effective.

In the processes of this invention, the sulfur is not merely physically dissolved by said compositions, but a chemical reaction occurs between the disulfide (or low rank polysulfide) and the sulfur, which results in the insertion of the sulfur into the sulfur-sulfur bond of the disulfide (or polysulfide of a low sulfur rank) to provide a polysulfide of a high sulfur rank.

PREFERRED EMBODIMENTS

A preferred embodiment of the composition of this invention includes a disulfide, a polysulfide or mixtures of these sulfides of the formula:

$$R^1SS_aSR^2$$

where $R^1$ and $R^2$ are independently $C_1$–$C_{24}$ alkyl and a is 0–3,

More preferably, where $R^1$ and $R^2$ are independently $C_1$–$C_4$ alkyl and a is 0–1.5, and still more preferably, $R^1$ and $R^2$ are methyl and a is 0–1.5. The most preferred embodiment uses dimethyl disulfide.

A preferred catalyst for the composition of this invention is a polyalkyleneoxydiamine of Formula 1, where $R^{3-7}$ are $CH_3$; $R^{8-9}$ are H; and x, y, and z are of any combination which produces a polyalkyleneoxyamine whose average molecular weight ranges from 200 to 6000. More preferably, the polyalkyleneoxyamine is as described by Formula 1 where $R^3$ and $R^7$ are $CH_3$, $R^{4-6}$ are H, $R^{8-9}$ are H, and x, y, and z are of any combination which produces a polyalkyleneoxyamine whose average molecular weight ranges from 200 to 6000. An even more preferred catalyst is a polyalkyleneoxyamine as described by Formula 1 where $R^{3-9}$ are H and x, y, and z are of my combination which produces a polyalkyleneoxyamine whose average molecular weight ranges from 200 to 6000.

The preferred, optionally added, aliphatic amine, aryl amine, alkaryl amine, or alkanolamine or their respective ethers which can be added to the above compositions have from 1 to 4 carbon atoms in the aliphatic or alkyl moieties; more preferably, they are dimethylaminoethanol, dimethylamino-2-propanol, diethylamine, triethylamine or mixtures thereof.

The following Examples are set forth to demonstrate the composition of this invention.

EXAMPLES

EXAMPLE 1

Compositions of dimethyl disulfide (DMDS) and a polyalkyleneoxyamine shown in Table 1 were bubbled with H₂S for 3 minutes to simulate sour gas well conditions, whereupon 3.5 g of sulfur were added at room temperature. The times were noted for the consumption of the sulfur. The superior sulfur-dissolving power of the composition of this Example 1, compared to the prior art composition of Hyne, set forth below Table 1, is clearly demonstrated.

TABLE 1

| DMDS (grams) | Polyalkyleneoxyamine* (microliters/milligrams) | Time (minutes) |
|---|---|---|
| 9.5 g | Jeffamine  T-403 (40 μl) | 1.77 |
| 9.5 g | Jeffamine ® C-346 (40 μl) | 4.55 |
| 9.5 g | Jeffamine ® D-230 (40 μl) | 1.10 |
| 9.5 g | Jeffamine ® D-2000 (40 μl) | 4.6 |
| 9.5 g | Jeffamine ® ED-600 (40 μl) | 0.68 |
| 9.5 g | Jeffamine ® ED-2001 (40 mg) | 1.37 |

*See identification of Jeffamine ® products previously set forth.

For the purpose of comparison, a mixture of sodium hydrosulfide (NaSH) and dimethylformamide (DMF) was prepared by adding the NaSH (0.015 g) to DMF (0.5 g) which had been first degassed with nitrogen. The resulting green mixture was then added to DMDS (9.5 g) after stirring for 1 hour. Sulfur (3.5 g) was subsequently added to the DMDS/DMF/NaSH mixture and a time of 10.17 minutes was noted for its consumption. Hyne reports a value of 5.83 minutes to take up 1 g of sulfur using the same composition. (ASRL Quarterly Bulletin, Vol. XIX, Nos. 1 & 2, 1982, p. 4). This comparative example serves as a standard prior art reference with which to compare the compositions of this invention. The formulation of this comparative example was not bubbled with H₂S since Hyne also reports that H₂S is not required as the mixture contains NaSH.

EXAMPLE 2

Compositions of dimethyl disulfide and a polyalkyleneoxyamine and a second amine (shown in Table 2) were bubbled with H₂S for 3 minutes to simulate sour gas well conditions, whereupon 3.5 g of sulfur were added at room temperature. The times were noted for the consumption of the sulfur, again demonstrating the superior sulfur-dissolving power of the compositions of this invention.

TABLE 2

| DMDS (grams) | Polyalklyeneoxyamine* (microliters) | Amine Number 2 (microliters) | Time (minutes) |
|---|---|---|---|
| 9.5 g | Jeffamine ® D-400 (20 µl) | None | 2.30 |
| 9.5 g | Jeffamine ® D-400 (20 µl) | Diethylamine (40 µl) | 1.30 |
| 9.5 g | Jeffamine ® D-400 (20 µl) | Triethylamine (40 µl) | 0.83 |
| 9.5 g | Jeffamine ® D-400 (20 µl) | Dimethylamino-2-propanol (20 µl) | 1.40 |
| 9.5 g | Jeffamine ® ED-600 (10 µl) | None | 3.55 |
| 9.5 g | Jeffamine ® D-400 (10 mg) | Dimethylaminoethanol (10 µl) | 2.03 |

*See identification of Jeffamine ® products previously set forth.

We claim:

1. A composition comprising a major proportion of a sulfide compound of the following formula:

$$R^1SS_aSR^2$$

where $R^1$ and $R^2$ are independently alkyl, alkaryl, alkoxyalkyl or hydroxyalkyl radicals wherein the alkyl moieties have from 1 to 24 carbon atoms, a is the average number of internal sulfur atoms in said sulfide and ranges from 0 to 3, and, in an amount sufficient to improve the activity of said sulfide for sulfur uptake, at least one polyalkyleneoxyamine or polyalkleneoxypolyamine containing a primary or secondary amine functionality and wherein the alkylene radical is a substituted or unsubstituted radical having from 2 to 4 carbon atoms exclusive of a substituent group.

2. The composition of claim 1 wherein aid polyalkyleneoxyamine or -polyamine are compounds having one of the following formulae:

where $R^3$, $R^4$, $R^5$, $R^6$, $R^7$, $R^{10}$, $R^{12}$, $R^{13}$, $R^{14}$, $R^{15}$, $R^{16}$, $R^{17}$, and $R^{18}$, are independently H, alkyl, alkaryl, hydroxyalkyl, alkoxyalkyl, haloalkyl wherein the alkyl moieties have from 1 to 20 carbon atoms, or phenyl radicals; $R^8$, $R^9$ and $R^{19}$ are independently H, alkyl, hydroxyalkyl, alkoxyalkyl, alkaryl wherein the alkyl moieties have from 1 to 10 carbon atoms, aryl or $CONH_2$; $R^{11}$ is the hydrocarbon residue of a triol; and b, c, d, e, f, g, h, x, y and z are independently values of 0–200, provided, however, that the total of such values in any single compound is no less than 2.

3. The composition of claim 1 wherein $R^1$ and $R^2$ are alkyl radicals.

4. The composition of claim 3 wherein a is 0 to 1.5.

5. The composition of claim 4 wherein $R^1$ and $R^2$ are methyl.

6. The composition of claim 5 wherein a is 0.

7. The composition of claim 1 additionally containing, in an amount sufficient to increase the activity of the composition to dissolve sulfur, an aliphatic amine, arylamine, alkarylamine, or ethers thereof wherein said amines are free of polyalkyleneoxy moieties and the aliphatic or alkyl moieties have from 1 to 24 carbon atoms.

8. The composition of claim 7 wherein the additional amine is dimethylaminoethanol.

9. The composition of claim 7 wherein the additional amine is dimethylamino-2-propanol.

10. The composition of claim 7 wherein the additional amine is triethylamine.

11. The composition of claim 7 wherein the additional amine is diethylamine.

12. The composition of claim 1 which additionally contains hydrogen sulfide, an alkyl, an alkaryl, a hydroxyalkyl or an alkoxyalkyl mercaptan where the alkyl moieties have from 1 to 24 carbon atoms, in an amount sufficient to enhance the ability of the composition to dissolve sulfur.

13. The composition of claim 12 which has been purged of residual hydrogen sulfide or mercaptan with an inert gas prior to the use of said composition.

14. The composition of claim 2 which additionally contains hydrogen sulfide, an alkyl, an alkaryl, a hydroxyalkyl or alkoxyalkyl mercaptan where the alkyl moieties have from 1 to 24 carbon atoms, in an amount sufficient to enhance the ability of the composition to dissolve sulfur.

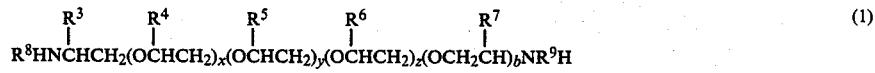

(1)

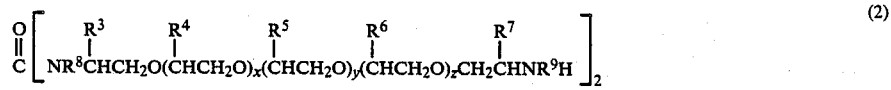

(2)

(3)

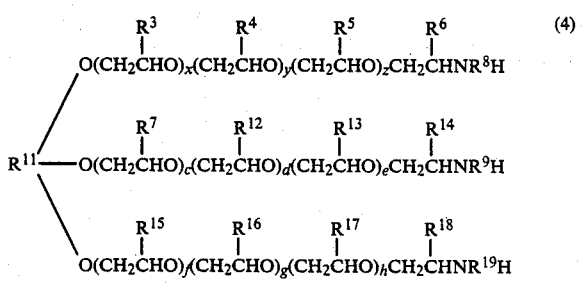

(4)

15. The composition of claim 14 which has been purged of residual hydrogen sulfide or mercaptan with an inert gas prior to the use of said composition.

16. The composition of claim 7 which additionally contains hydrogen sulfide, an alkyl, an alkaryl, a hydroxyalkyl and an alkoxyalkyl mercaptan where the alkyl moieties have from 1 to 24 carbon atoms, in an amount sufficient to enhance the ability of the composition to dissolve sulfur.

17. The composition of claim 16 which has been purged of residual hydrogen sulfide or mercaptan with an inert gas prior to the use of said composition.

18. A method of preventing or removing sulfur plug formation in a system containing sulfur comprising passing into said system, in an amount sufficient to dissolve sulfur, a composition comprising a major proportion of a sulfide compound of the following formula:

$$R^1SS_aSR^2$$

where $R^1$ and $R^2$ are independently alkyl, alkaryl, alkoxyalkyl or hydroxyalkyl radicals wherein the alkyl moieties have from 1 to 24 carbon atoms, a is the average number of internal sulfur atoms in said sulfide and ranges from 0 to 3, and, in an amount sufficient to improve the activity of said sulfide for sulfur uptake, at least one polyalkyleneoxyamine or polyalkyleneoxypolyamine containing a primary or secondary amine functionality and wherein the alkylene radical is a substituted or unsubstituted radical having from 2 to 4 carbon atoms exclusive of a substituent group.

19. The method of claim 18 wherein said system is an oil or gas well.

20. The method of claim 19 wherein said polyalkyleneoxyamine or -polyamine is a compound of the following formulae:

$$R^8HNCHCH_2(OCHCH_2)_x(OCHCH_2)_y(OCHCH_2)_z(OCH_2CH)_bNR^9H \quad (1)$$
$$\overset{R^3}{|} \quad \overset{R^4}{|} \quad \overset{R^5}{|} \quad \overset{R^6}{|} \quad \overset{R^7}{|}$$

$$\overset{O}{\underset{C}{\parallel}}\left[NR^8CHCH_2O(CHCH_2O)_x(CHCH_2O)_y(CHCH_2O)_zCH_2CHNR^9H\right]_2 \quad (2)$$

$$R^{10}O(CH_2CHO)_x(CH_2CHO)_y(CH_2CHO)_zCH_2CHNR^8H \quad (3)$$

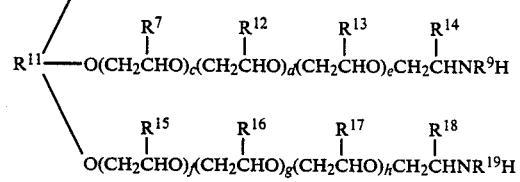  (4)

where $R^3$, $R^4$, $R^5$, $R^6$, $R^7$, $R^{10}$, $R^{12}$, $R^{13}$, $R^{14}$, $R^{15}$, $R^{16}$, $R^{17}$, and $R^{18}$, are independently H, alkyl, alkaryl, hydroxyalkyl, alkoxyalkyl, haloalkyl wherein the alkyl moieties have from 1 to 20 carbon atoms, or phenyl radicals; $R^8$, $R^9$ and $R^{19}$ are independently H, alkyl, hydroxyalkyl, alkoxyalkyl, alkaryl wherein the alkyl moieties have from 1 to 10 carbon atoms, aryl or $CONH_2$; $R^{11}$ is the hydrocarbon residue of a triol; and b, c, d, e, f, g, h, x, y and z are independently values of 0–200, provided, however, that the total of such values in any single compound is no less than 2.

21. The method of claim 19 wherein said composition additionally contains, in an amount sufficient to increase the activity of the composition to dissolve sulfur, an aliphatic amine, aryl amine, alkaryl amine, or ethers thereof wherein said amines are free of polyalkyleneoxy moieties and the aliphatic or alkyl moieties have from 1 to 24 carbon atoms.

22. The method of claim 18 wherein said system comprises a pipe subject to such formation.

23. The method of claim 22 wherein said polyalkyleneoxyamine or -polyamine is a compound of the following formulae:

$$R^8HNCHCH_2(OCHCH_2)_x(OCHCH_2)_y(OCHCH_2)_z(OCH_2CH)_bNR^9H \quad (1)$$
$$\overset{R^3}{|} \quad \overset{R^4}{|} \quad \overset{R^5}{|} \quad \overset{R^6}{|} \quad \overset{R^7}{|}$$

$$\overset{O}{\underset{C}{\parallel}}\left[NR^8CHCH_2O(CHCH_2O)_x(CHCH_2O)_y(CHCH_2O)_zCH_2CHNR^9H\right]_2 \quad (2)$$

(3)

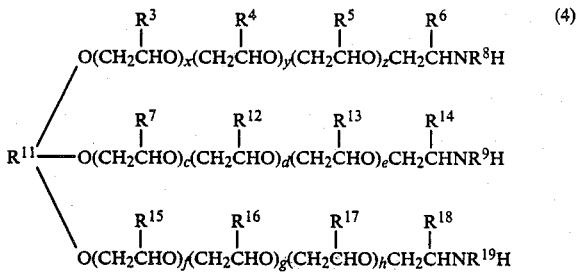(4)

where $R^3$, $R^4$, $R^5$, $R^6$, $R^7$, $R^{10}$, $R^{12}$, $R^{13}$, $R^{14}$, $R^{15}$, $R^{16}$, $R^{17}$, and $R^{18}$, are independently H, alkyl, alkaryl, hydroxyalkyl, alkoxyalkyl, haloalkyl wherein the alkyl moieties have from 1 to 20 carbon atoms, or phenyl radicals; $R^8$, $R^9$ and $R^{19}$ are independently H, alkyl, hydroxyalkyl, alkoxyalkyl, alkaryl wherein the alkyl moieties have from 1 to 10 carbon atoms, aryl or $CONH_2$; $R^{11}$ is the hydrocarbon residue of a triol; and b, c, d, e, f, g, h, x, y and z are independently values of 0–200, provided, however, that the total of such values is no less than 2.

24. The method of claim 22 wherein said composition additionally contains, in an amount sufficient to increase the activity of the composition to dissolve sulfur, an aliphatic amine, arylamine, alkaryl amine, or ethers thereof wherein said amines are free of polyalkyleneoxy moieties and the aliphatic or alkyl moieties have from 1 to 24 carbon atoms.

* * * * *